United States Patent
Bryant

(10) Patent No.: US 10,845,281 B1
(45) Date of Patent: *Nov. 24, 2020

(54) METHOD FOR TESTING A PROPPANT

(71) Applicant: Matthew D. Bryant, Charlotte, NC (US)

(72) Inventor: Matthew D. Bryant, Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/358,789

(22) Filed: Mar. 20, 2019

Related U.S. Application Data

(63) Continuation of application No. 15/625,817, filed on Jun. 16, 2017, now Pat. No. 10,281,380.

(60) Provisional application No. 62/351,774, filed on Jun. 17, 2016.

(51) Int. Cl.
  *G01N 3/12* (2006.01)
  *G01N 15/02* (2006.01)
  *G01N 33/00* (2006.01)
  *G01M 3/00* (2006.01)

(52) U.S. Cl.
  CPC ............ *G01N 3/12* (2013.01); *G01M 3/00* (2013.01); *G01N 15/0272* (2013.01); *G01N 33/00* (2013.01)

(58) Field of Classification Search
  CPC .. G01N 3/00; G01N 3/08; G01N 3/12; G01N 15/00; G01N 15/02; G01N 15/0272
  See application file for complete search history.

(56) References Cited

U.S. PATENT DOCUMENTS

| | | |
|---|---|---|
| 4,581,253 A | 4/1986 | Evans et al. |
| 7,562,583 B2 | 7/2009 | Conway et al. |
| 7,654,353 B2 | 2/2010 | Dubose et al. |
| 7,790,656 B2 | 9/2010 | Windebank et al. |
| 8,022,019 B2 | 9/2011 | Rush et al. |
| 8,075,997 B2 | 12/2011 | Smith et al. |
| 8,127,849 B2 | 3/2012 | Gupta |
| 8,133,587 B2 | 3/2012 | Rediger et al. |
| 8,685,902 B2 | 4/2014 | Pershikova et al. |
| 8,865,631 B2 | 10/2014 | Eldred et al. |
| 10,281,380 B1 | 5/2019 | Bryant |
| 2009/0306898 A1 | 12/2009 | Anschutz |
| 2010/0313645 A1 | 12/2010 | Doman et al. |
| 2014/0037962 A1 | 2/2014 | Moore et al. |
| 2016/0047729 A1 | 2/2016 | Libasci |

OTHER PUBLICATIONS

Getty, J.; Bulau, CR. "Are the Laboratory Measurements of Proppant Crush Resistance Unrealistically Low?" SPE; Apr. 13, 2014.
(Continued)

*Primary Examiner* — Nguyen Q. Ha
(74) *Attorney, Agent, or Firm* — Roy Kiesel Ford Doody & North, APLC; Chad A. Grand

(57) ABSTRACT

In the specification and drawings a method for testing a proppant is described and shown that involves: obtaining a proppant sample; separating the proppant sample into a plurality of sub-samples according to grain size; subjecting each sub-sample to a pressure that is sufficient to crush at least a portion of the proppant within at least one of the plurality of sub-samples; and independently analyzing each sub-sample to determine at least one of: i) the amount of proppant that was crushed within each sub-sample; and ii) the amount of proppant that was not crushed within each sub-sample.

20 Claims, 4 Drawing Sheets

(56) References Cited

OTHER PUBLICATIONS

Palisch, Terry; Duenckel, R; Chapman, Mark; Woolfold, Scott; Wincent, M.C.; "How to Use and Misuse Proppant Crush Tests: Exposing the top 10 Myths" SPE; Insight Consulting; Aug. 1, 2010.

METHOD FOR TESTING A PROPPANT

I. CROSS-REFERENCE TO RELATED APPLICATION

This application claims the benefit of U.S. Non-provisional application Ser. No. 15/625,817, filed Jun. 16, 2017, which claims the benefit of U.S. Provisional Application 62/351,774, filed Jun. 17, 2016, which are hereby incorporated by reference in their entirety.

II. STATEMENT REGARDING FEDERALLY SPONSORED RESEARCH OR DEVELOPMENT

Not Applicable.

III. THE NAMES OF THE PARTIES TO A JOINT RESEARCH AGREEMENT

Not Applicable.

IV. INCORPORATION-BY-REFERENCE OF MATERIAL SUBMITTED ON A COMPACT DISC

Not Applicable.

V. FIELD

An embodiment of the invention involves a method of testing a proppant, such as sand, which can be used, for example, in the hydraulic fracturing industry.

VI. BACKGROUND

In the hydraulic fracturing ("fracking") process, it can be desirable that oil and gas operators and the pumping companies that they employ have a full and transparent understanding of the proppant that they are using in the fracking process.

Hydraulic fracturing is the method by which large amounts of proppant, chemicals and water are forced beneath the earth. Fractures are produced in shale deep beneath the earth, and oil/gas that was once trapped is now free to flow.

Proppant, which is the term used to describe the product used to "prop" open the fractures deep within the earth, comes in three main categories: raw fracking sand, resin coated fracking sand, and ceramic proppant. Raw fracking sand is generally considered to be the most widely used. The testing methodology described herein can be applied to all three categories. The testing methodology described herein can also have other uses and benefits.

One aspect of a particular sand product (that is fit for use in fracking) that may be desirable to know is its strength. Sand can be found all over the world, but not every sand grain is created equal. Some sand is much stronger than others, and it is the stronger sands that are usually the most desirable for use in fracking. Strength can be important because it is often desirable that the grains of sand keep the fractures "propped" open to allow oil and gas to flow. If the sand is too weak, it will fracture, break, and/or crush under the enormous pressure beneath the earth, and this in turn will hinder the flow of oil and gas.

Ideally, in a fracking operation, every grain of sand would stay exactly the same, even under enormous amounts of pressure. In other words a grain of sand would not break or crush at all. Ideally, every grain of sand would maintain its original form.

The current testing method is to not test each individual grain size of proppant within a given sample of proppant, but to instead test all of the various grain sizes together. The 25, 30, 35 and 40 mesh sizes of proppant are all placed into a crush cell and pressed together. After the proppant is pressed, the proppant is sieved again using only a sieve having a 40 mesh and pan. The result of this test provides the percentage of material that falls below a sieve having a 40 mesh size and the percentage of material that remains above a sieve having a 40 mesh size.

This method does not give an accurate account of sand that actually broke, chipped, crushed (or otherwise changed in any way). This is because a grain of sand can chip yet the larger portion may not fall below the 40 mesh screen.

The current method generally does not provide a clear score for the proppant to be for decision making purposes, and it generally does not provide an accurate account of the proppant's ability maintain its original form.

An embodiment of the invention disclosed herein can provide a clear and transparent result. An embodiment of the invention can allow users to see if a particular proppant product can maintain its original form under certain amounts of pressure. In other words, a testing method described herein can provide a highly accurate estimate as to what percentage of the proppant will not break or crush in any way.

An example result of an embodiment of a test described herein would be the following:

At 5,000 PSI, the proppant maintained 92.3% of its original form.

At 6,000 PSI the proppant maintained 75.5% of its original form.

VII. SUMMARY

An embodiment of the invention is a method of testing the crush strength of sand to determine its suitability for hydraulic fracturing. Currently within the industry, the crush strength of sand is determined by testing all sand within a given type (e.g. "20/40" sand) in a single crush test. That is, a single sample of a type of sand (e.g. 20/40 sand) containing multiple sand grain sizes (e.g. 25, 30, 35, and 40 sieve sizes) is subjected to a pressure (e.g. 6,000 PSI). After the single sample is subjected to pressure, the entire sample of sand is then sieved over the smallest sieve size (40 sieve size in this example), and the amount of sand that passes through the 40 sieve is measured to determine the amount of sand that was crushed.

Instead of simply taking a single sample of sand that contains multiple sand grain sizes and subjecting it to a single pressure test and then subsequently a single sieving to determine the amount of sand that was crushed, an embodiment of the current invention performs a crush test on every sieve size within a single sample of sand. For example a sample of 20/40 sand would first be sorted into multiple separate sub-samples according to grain size (e.g. separate sub-samples for each of 25, 30, 35, and 40 grain sizes) and each individual sub-sample (each of which contain a different grain size) would be separately subjected to a pressure (e.g. 6,000 PSI). After each individual sub-sample is subjected to pressure, each of the individual sub-samples are then separately sieved over the sieve size that corresponds to that sub-sample (e.g. the 25 grain size sub-sample is sieved over the 25 sieve, the 30 grain size sub-sample is sieved over the 30 sieve, etc.). The amount of sand that passes through the respective sieve for each sub-sample is then separately measured to determine the amount of sand that was crushed for each sub-sample. Next, a weighted average of the amount of sand that was crushed for the sub-samples can be calculated to give a representative score for the entire sample of the 20/40 sand. A potential advantage of this approach is that there is no way for sand that has broken in any way to "hide" above the smallest sieve (in this example, the 40 sieve). The test can allow for full transparency. The current industry testing may show that 92% of the sand remained above the 40 sieve (8% below), while an embodiment of the invention described herein may show, for example, that only 60% of the sand remained in its original form with no breakage at all (meaning 40% had some breakage). It can be desirable for the Hydraulic fracturing industry to know what percentage of sand being used will maintain its original form, and an embodiment of this invention can do that.

As opposed to or in addition to using a sieve to separate and/or determine sand grain sizes, other procedures and/or apparatuses may be used. For example, an optical analyzer or other analyzer may be may be used.

VIII. BRIEF DESCRIPTION OF THE SEVERAL VIEWS OF THE DRAWINGS

IX. DETAILED DESCRIPTION

Figure 1:
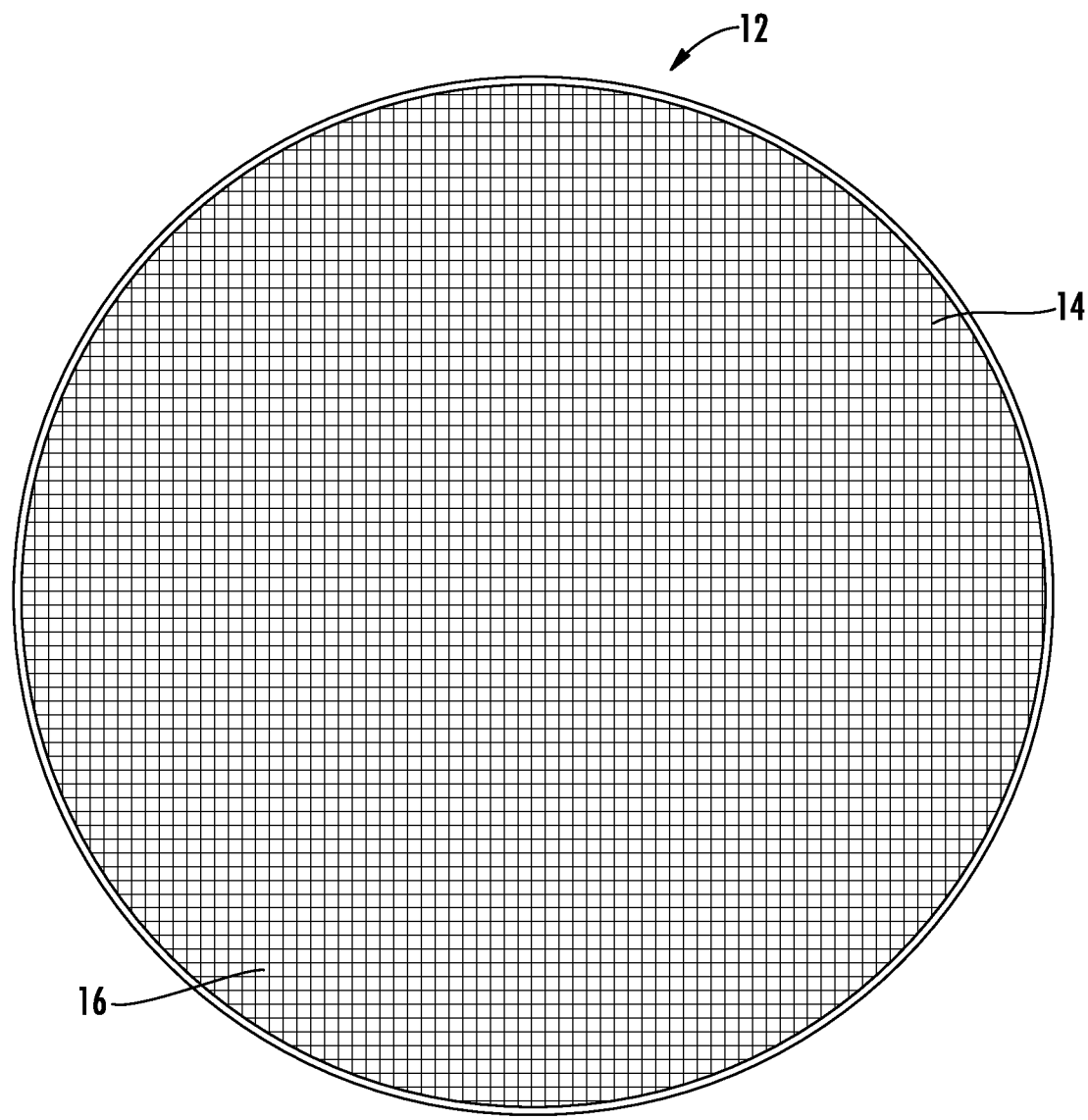
FIG. 1 is a top view of a sieve.

As required, detailed embodiments of the present invention are disclosed herein. However, it is to be understood that the disclosed embodiments are merely exemplary of the invention, which can be embodied in various forms. As such, any feature(s) used in one embodiment can be used in another embodiment. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The terms "connected" and/or "coupled," as used herein, are defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the present invention. Referring now to FIGS. 1 to 4, exemplary embodiments of a method of testing proppant can be used, for example, to determine the strength of the proppant and/or to determine the suitability of the proppant for use in hydraulic fracturing (fracking). A proppant is a material which can be used to keep an induced hydraulic fracture open. A proppant is typically a solid material, such as sand, treated sand, or ceramic materials. In the embodiments shown in FIGS. 2, 3A, and 3B, the proppant is a grain of sand 10. It can be desirable to know the strength of a proppant to, for example, determine its suitability for use in fracking. It is often desirable that the proppant be strong enough to keep the induced hydraulic fracture open. If the proppant is not strong enough, it will be crushed under the high pressure beneath the surface of the earth, which can hinder the flow of oil and gas. As used herein, a grain of proppant is "crushed" if it breaks, fractures, chips, or permanently changes shape and/or dimensions.

Sand types used in fracking can include for example, 12/20, 16/30, 20/40, 30/50, 40/70, and 70/140 sand. Of these, 12/20 is the coarsest (or largest) sand. 70/140 sand is the finest (or smallest) sand. The choice of a sand to be used in a fracking operation is often determined by the engineer designing the well, who often takes into consideration a host of factors when making a decision. Generally speaking, it is not uncommon for multiple products to be used in one well. For example 40/70 sand and 70/140 sand may be used in the fracking of one well.

Figure 2:
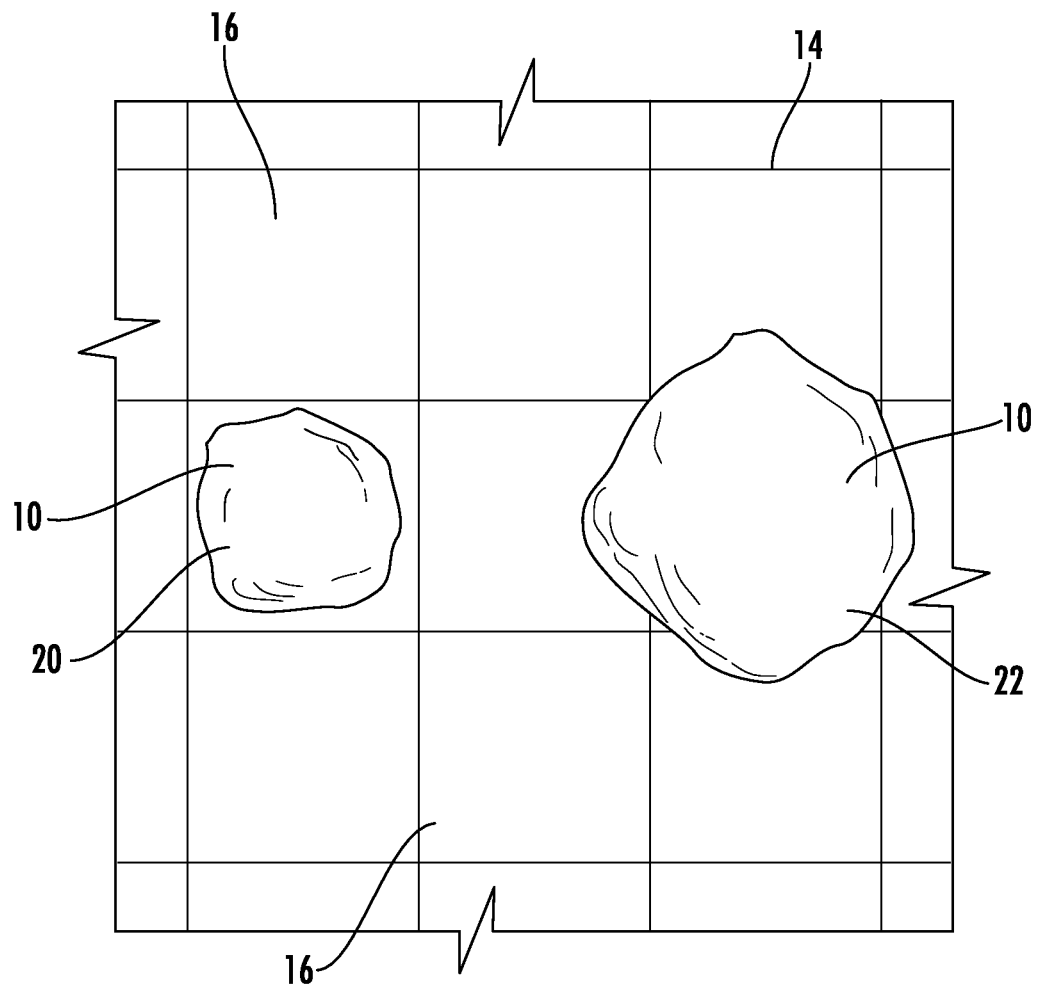
FIG. 2 is a top view of the mesh of a sieve, as well as two grains of sand.
Figure 3A:
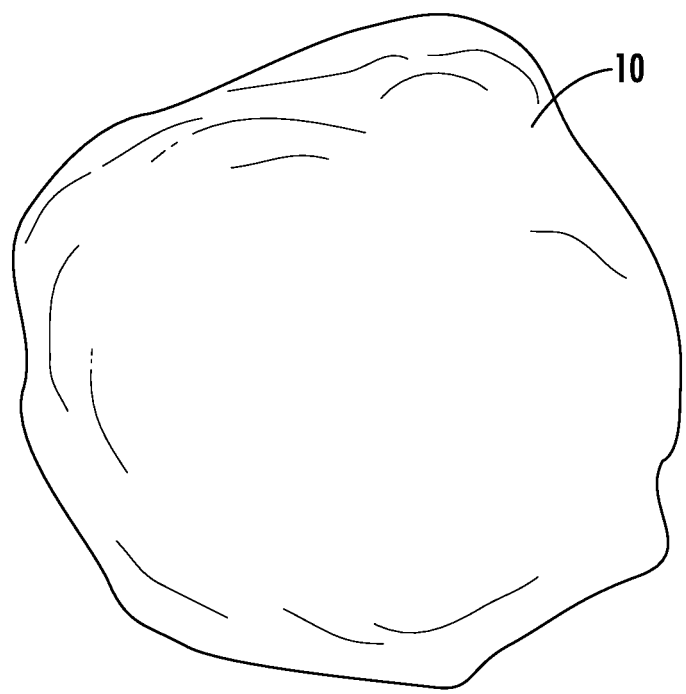
FIG. 3A is a side view of a grain of sand.
Figure 3B:
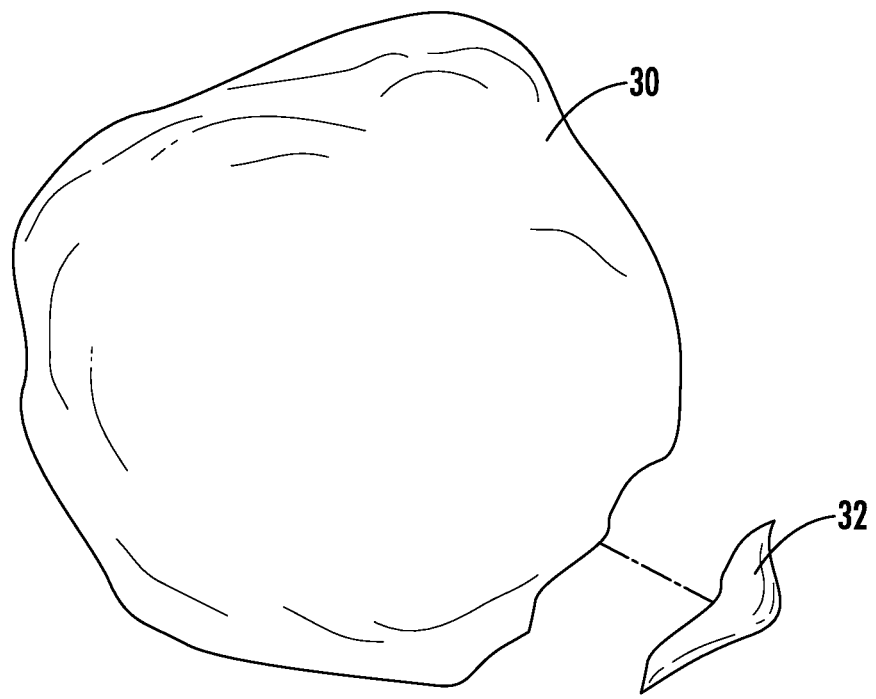
FIG. 3B is a side view of a grain of sand.

In an embodiment of the invention, in order to test a proppant, a sample of proppant is first obtained. A sample of proppant contains a number of grains/particles of proppant, such as grains of sand 10, as shown in FIGS. 2, 3A, and 3B. Grains of sand within a proppant sample often vary in size, with the various sizes often failing within a range. In an embodiment, a type of sand that can constitute a proppant sample is known as "20/40" sand. In a proppant sample comprised of "20/40" sand, all of the grains of sand will pass through a sieve having a 20 mesh size, but none of the grains of sand will pass through a sieve having a 40 mesh size. In such a sample, the grains of sand often vary in size between 20 and 40 mesh sizes. For example, a proppant sample comprised of 20/40 sand can consist of sand having 25, 30, 35, and 40 mesh sizes.

The number in the mesh size of a sieve, such as the "25" in a sieve having a 25 mesh size, or the "40" in a sieve having a 40 mesh size, can refer to the number of openings there are per linear inch in the mesh of a sieve. The following chart provides examples of the size of the openings in the mesh for sieves of various mesh size:

| Mesh Size Of Sieve | Opening in Millimeters | Opening in Inches |
|---|---|---|
| No. 3½ | 5.66 | 0.233 |
| No. 4 | 4.76 | 0.187 |
| No. 5 | 4.00 | 0.157 |
| No. 6 | 3.36 | 0.132 |
| No. 7 | 2.83 | 0.111 |
| No. 8 | 2.38 | 0.0937 |
| No. 10 | 2.00 | 0.0787 |
| No. 12 | 1.68 | 0.0661 |
| No. 14 | 1.41 | 0.0555 |
| No. 16 | 1.19 | 0.0469 |
| No. 18 | 1.00 | 0.0394 |
| No. 20 | 0.841 | 0.0331 |
| No. 25 | 0.707 | 0.0278 |
| No. 30 | 0.595 | 0.0234 |
| No. 35 | 0.500 | 0.0197 |
| No. 40 | 0.420 | 0.0165 |
| No. 45 | 0.354 | 0.0139 |
| No. 50 | 0.297 | 0.0117 |
| No. 60 | 0.250 | 0.0098 |
| No. 70 | 0.210 | 0.0083 |
| No. 80 | 0.177 | 0.0070 |
| No. 100 | 0.149 | 0.0059 |
| No. 120 | 0.125 | 0.0049 |
| No. 140 | 0.105 | 0.0041 |
| No. 170 | 0.088 | 0.0035 |
| No. 200 | 0.074 | 0.0029 |
| No. 230 | 0.063 | 0.0025 |
| No. 270 | 0.053 | 0.0021 |
| No. 325 | 0.044 | 0.0017 |
| No. 400 | 0.037 | 0.0015 |

A sieve having a 20 mesh size has larger openings in the mesh than does a sieve having a 40 mesh size, therefore a sieve having a 20 mesh size is considered to have a larger mesh size than does a sieve having a 40 mesh size.

Referring to FIGS. 1 and 2, a sieve 12 is shown. The sieve 12 has a grid of mesh 14, the mesh 14 can have openings 16 that are sized as desired in order to allow grains of proppant of a certain sufficiently small size to pass through the openings 16, while not allowing grains of proppant of a larger size to pass through the openings 16. For example, during a sieving procedure of a sample of proppant, grains of proppant that are smaller than the openings 16 in the mesh 14 can pass through the openings 16, but grains of proppant that are larger than the openings 16 in the mesh 14 cannot pass through the openings 16 and thus will remain on top of the mesh 14 of the sieve 12.

Referring to FIG. 2, the proppant is a grain of sand 10. The smaller grain of sand 20 is small enough to pass through the openings 16 in the mesh 14, but the larger grain of sand 22 is too large to pass through the openings 16 in the mesh 14. During a sieving of a proppant sample or of a proppant sub-sample, sand grain 20 will pass through the openings 16 in the mesh 14, while sand grain 22 will not pass through the openings 16 in the mesh 14 and therefore will remain on top of the mesh 14.

Currently within the industry, a common method of testing a proppant to determine the crush strength of the grains of proppant, such as sand grain 10, involves testing all of the various grain sizes of sand 10 within a given type (e.g. 20/40 sand) in a single crush test. That is, a single proppant sample of a type of sand (e.g. 20/40 sand) containing multiple sizes of sand grains 10 (e.g. 25, 30, 35, and 40 mesh sizes) is subjected to a pressure. After the single proppant sample is subjected to pressure, the entire proppant sample is then sieved over a sieve having a mesh size corresponding to the smallest size of sand grain that existed in the proppant sample prior to the proppant sample being subjected to a pressure (in this example, that would be a sieve having a 40 mesh size).

Next, in this example of a common method of testing a proppant in the industry, the amount of sand that passes through the sieve having a 40 mesh size is measured to determine the amount of sand that was crushed. This method of testing a proppant has aspects to it that some would consider to be disadvantages. For example, the amount of sand that was actually crushed is not accurately represented by what passes through a sieve having a 40 mesh size. Instead, the amount of sand that passes through a sieve having a 40 mesh size can grossly underestimate the amount of sand that was actually crushed.

Continuing with this example, and referring to FIGS. 3A and 3B, a sand grain that is size 25 (meaning it is small enough to pass through a sieve having a 20 mesh size, yet too large to pass through a sieve having a 25 mesh size and therefore it remains on top of a sieve having a 25 mesh size during a sieving procedure) can crush, but some of the broken pieces of the sand grain may still be too large to pass through the openings in the mesh of a sieve having a 40 mesh size. For example, FIG. 3A shows a single grain of sand 10. Referring to FIGS. 3A and 3B, during a crush test, the grain of sand may break into two sub-grain pieces, with one of the sub-grain pieces 30 being almost the size of the original sand grain 10, and with the other sub-grain piece 32 being much smaller than the original sand grain and essentially constituting nothing more than a small chip off of the original sand grain 10. In this instance, even though the original size 25 sand grain 10 was crushed, the larger sub-grain piece 32 is still too large to pass through a sieve having a 40 mesh size. Therefore, in this example of a common method of testing a proppant in the industry, the test simply shows the amount of sand that was small enough to pass through a sieve having a 40 mesh size. The test does not give an accurate representation of the amount of sand that was actually crushed. The amount of sand that is small enough to pass through a sieve having a 40 mesh size and the amount of sand that was actually crushed can be very different.

Instead of simply taking a single proppant sample that contains sand grains of multiple sizes and subjecting the entire proppant sample to a single pressure test and then subsequently a single sieving to determine the amount of sand that was crushed, an embodiment of the invention is a method of testing a proppant by performing separate crush tests on each size of the various sizes of sand grains that exist in a proppant sample. Because separate crush tests are performed on each size of the various sizes of sand grains that exist in a proppant sample, a sand grain of for example 25 size that is crushed but that retains most of its original size, such as sand sub-grain piece 30, will be detected in the crush test.

An embodiment of a method of testing a proppant can involve one or more of the following procedures or steps:

1) Distribution of Sample—In an embodiment of a method of testing a proppant that is composed of 20/40 sand, the first step is to find the distribution of the 20/40 sample that is going to be tested. This can be accomplished by:
   a. Splitting entire sample of proppant down to 100 gram proppant sample.
   b. Stacking sieves having 20, 25, 30, 35, 40, mesh sizes and pan on top of each other.
   c. Securing the stacked sieves to a vibration machine.
   d. Pouring the 100 gram proppant sample into the top of the stacked sieves.
   e. Running the vibration machine for 10 minutes.
   f. Weighing the amount of sand on each sieve
   g. Once the amount of sand on every sieve has been weighed, converting each weight to a percentage of the 100 gram proppant sample.
      i. For example, if the weight of sand on a sieve having a 25 mesh size is 30 grams, the percentage of the 100 gram proppant sample is 30% (30 grams/100 grams=30%).
   h. In this example, the distribution of the proppant sample is found to be:
   20 Sieve: 0%
   25 Sieve: 30%
   30 Sieve: 25%
   35 Sieve: 30%
   40 Sieve: 15%
   PAN: 0%
2) Perform a Crush Test on each individual sieve size
   a. Test 25 Mesh sand
      i. Take 50 grams of 25 mesh sand
         1. Note—in an embodiment, step 1 (a.-f.) can be performed in order to get 50 grams of each sieve size.
      ii. Pouring the sand into a crush cell, and placing a piston-like tube/metal insert on top.
      iii. Placing the loaded crush cell into the press.
      iv. Using the press to apply 6,000 PSI of pressure to the crush cell (in this example, it is assumed that a customer has requested to test the sand strength at 6,000 PSI).
      v. After the pressure has been released, removing the crush cell from the press and performing another sieve analysis using only the 25 sieve and the pan.
         1. Stacking the 25 sieve and the pan together.
         2. Securing the sieve and pan to the vibration machine.
         3. Pouring the contents of the crush cell into the 25 sieve.
         4. Running the vibration machine for 10 minutes.
         5. Weighing the amount of sand in the 25 sieve.
         6. Weighing the amount of sand in the pan.
         7. Converting each weight to a percentage of the whole.
            a. In this example the distribution was found to be:
            25 sieve: 68%
            Pan: 32%
            It can be concluded from this analysis that approximately 68% of the 25 mesh sand in this sample maintained its form. (This is known because before the 25 mesh sand was placed in the crush cell and pressed, the distribution was 100% 25 mesh).
   b. Test 30 Mesh (same procedure as step 2a. above)
   c. Test 35 Mesh (same procedure as step 2a. above)
   d. Test 40 Mesh (same procedure as step 2a. above)
3) Calculate Final Proppant Score
   a. In this example, after conducting a crush test on each individual sieve size, these are the results of those tests:
      i. 25 mesh: 68% maintained form
      ii. 30 mesh: 72% maintained form
      iii. 35 mesh: 79% maintained form
      iv. 40 mesh: 89% maintained form
   b. To get a final score for the proppant sample, a weighted average for the sample as a whole can be calculated (refer back to step 1h. to get sieve distribution)
      i. 25 mesh: (68% maintained)×(30% of this mesh in final product)=20.4%
      ii. 30 mesh: (72% maintained)×(25% of this mesh in final product)=18.0%
      iii. 35 mesh: (79% maintained)×(30% of this mesh in final product)=23.7%
      iv. 40 mesh: (89% maintained)×(15% of this mesh in final product)=13.4%
   TOTAL: 75.5%
   c. Proppant Score=75.5
      i. Based on this analysis, it can be concluded that approximately 75.5% of this sample will maintain its original form when subjected to 6,000 PSI.

Figure 4:
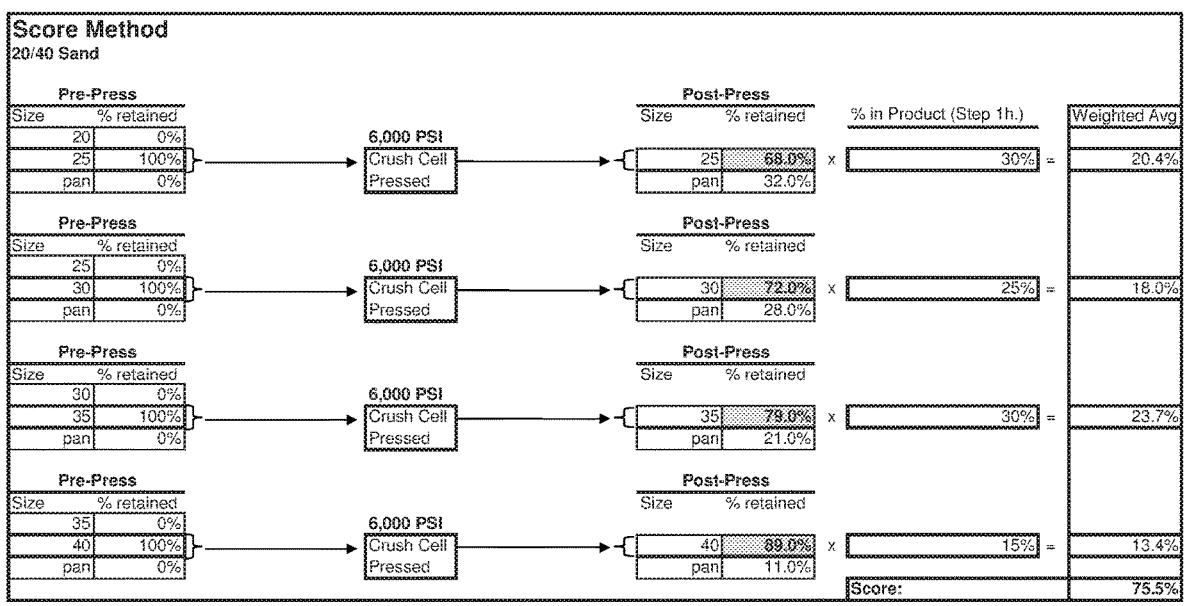
FIG. 4 is a chart showing certain aspects of an embodiment described herein.

Various aspects of steps 2 and 3 are also shown in FIG. 4. Also, as noted in FIG. 4, the percentage values from step 1h above are used in the example calculations shown in FIG. 4.

In operation of an embodiment of the invention, a method of testing a proppant can first involve obtaining a proppant sample that contains grains of proppant, such as sand grain 10, of various sizes. Next the amount of the proppant sample can be determined, such as by weighing the proppant sample or counting the grains 10 of proppant in the proppant sample.

The proppant sample is then separated into a plurality of sub-samples according to grain size. For example, in an embodiment, an optical analyzer can be used to separate the proppant sample into a plurality of sub-samples according to grain size. In another embodiment, sieves of various mesh sizes can be used to separate the proppant sample into a plurality of sub-samples according to grain size.

In an embodiment, the proppant sample can be separated into a plurality of sub-samples according to grain size by first combining a plurality of sieves 12 having various mesh sizes into a stack of sieves, such that the plurality of sieves 12 within the stack are arranged according to mesh size with the ordering of the plurality of sieves 12 proceeding from the sieve having a largest mesh size at a top of the stack, to the sieve having a smallest mesh size at a bottom of the stack. For example, the plurality of sieves can be comprised of a sieve having a 20 mesh size, a sieve having a 25 mesh size, a sieve having a 30 mesh size, a sieve having a 35 mesh size, and a sieve having a 40 mesh size. In this example, in the stack of sieves, the sieve having a 35 mesh size is stacked on top of the sieve having a 40 mesh size, the sieve having a 30 mesh size is stacked on top of the sieve having a 35 mesh size, the sieve having a 25 mesh size is stacked on top of the sieve having a 30 mesh size, and the sieve having a 20 mesh size is stacked on top of the sieve having a 25 mesh size.

Next, the proppant sample can be deposited into the top of the stack of sieves, such as by placing, pouring, or otherwise locating the proppant sample into the sieve 12 at the top of the stack of sieves. The stack of sieves is then vibrated so all of the grains of proppant that are small enough to pass through one or more of the sieves do in fact pass through each of the sieves that the a given grain of proppant is small enough to pass through. In an embodiment, a machine, such a sieve vibrator, can be used to vibrate the stack of sieves, and the stack of sieves can be vibrated for a period of time, such as ten minutes. In an embodiment, the proppant sample is then separated into a plurality of pre-pressure subjected sub-samples by removing the portion of the proppant sample that remained on each respective sieve 12 of the plurality of sieves subsequent to vibrating the stack of sieves, with each of the plurality of pre-pressure subjected sub-samples corresponding to the portion of the proppant sample that remained on each respective sieve 12 of the plurality of sieves subsequent to vibrating the stack of sieves.

Next in the operation of an embodiment of the invention, the amount of each pre-pressure subjected sub-sample is measured to determine a pre-pressure subjected sub-sample value for each pre-pressure subjected sub-sample. A pre-pressure subjected sub-sample value can include, for example, the weight of the pre-pressure subjected sub-sample, the percentage of the original proppant sample that the pre-pressure subjected sub-sample constitutes, as well as other measurements or values.

Each pre-pressure subjected sub-sample is then subjected to a pressure, resulting in a corresponding post-pressure subjected sub-sample for each pre-pressure subjected sub-sample. Each pre-pressure subjected sub-sample can be subjected to a pressure by, for example, separately placing each pre-pressure subjected sub-sample into a crush cell, inserting a metal insert into the crush cell, and then using a press or other apparatus to apply a specified force, such as a force of about 6,000 PSI, to the crush cell. In an embodiment, the specified force is sufficient to crush at least a portion of the proppant within at least one of the plurality of pre-pressure subjected sub-samples.

Next, each of the plurality of sieves is separately stacked over a pan, such that a distinct sieve-pan stack is formed. Said another way, each of the distinct sieve-pan stacks has a pan on the bottom, with a sieve stacked on top of the pan. In an embodiment, this can be accomplished by having a separate pan for each of the plurality of sieves. In another embodiment, this can be accomplished by using a single pan, and first using that pan to form the first sieve-pan stack, and then removing that pan from the first sieve-pan stack and using it to form the second sieve-pan stack, and so on.

Each respective post-pressure subjected sub-sample is then returned to its corresponding sieve of said plurality of sieves. In other words, the sieve that a given pre-pressure subjected sub-sample is removed from prior to subjecting the sub-sample to pressure, is the same sieve that the post-pressure subjected sub-sample is returned to after it has been subjected to pressure.

Next, each of the sieve-pan stacks is vibrated so that all of the grains of proppant that are small enough to pass through the sieve do in fact pass through the sieve and become deposited in the pan, such as by falling into the pan.

The vibrating of the sieve-pan stacks can be performed in a manner similar to the vibrating of the stack of sieves discussed above.

A post-pressure subjected sub-sample value can then be determined for each post-pressure subjected sub-sample. The determination of this value can be accomplished by measuring at least one of: i) the amount of each post-pressure subjected sub-sample that remained on the sieve of a given distinct sieve-pan stack; and ii) the amount of that post-pressure subjected sub-sample that was deposited in the pan of that given distinct sieve-pan stack. For example, the weight of the portion of each post-pressure subjected sub-sample that remained on the sieve of a given distinct sieve-pan stack can be measured, and/or the weight of the portion of that post-pressure subjected sub-sample that was deposited in the pan of that given distinct sieve-pan stack can be measured. As opposed to or in addition to determining a post-pressure subjected sub-sample value for each post-pressure subjected sub-sample, after each sub-sample is subjected to pressure, each sub-sample can be independently analyzed to determine at least one of: i) the amount of proppant that was crushed within each sub-sample; and ii) the amount of proppant that was not crushed within each sub-sample. The analysis can be performed by weighing the sub-sample, optically analyzing the sub-samples, or by any other means. Similarly, as opposed to or in addition to determining a post-pressure subjected sub-sample value for each post-pressure subjected sub-sample, after each sub-sample is subjected to pressure, each sub-sample can be measured to determine at least one of: i) the amount of proppant that passes through the respective sieve for each sub-sample; and ii) the amount of proppant that remained on the respective sieve for each sub-sample; and in an embodiment this measurement(s) can be used to determine the amount of proppant that was crushed for each sub-sample.

At this point in an embodiment of a method of testing a proppant, a number of things can happen next. For example, in an embodiment, each post-pressure subjected sub-sample value can be compared to its pre-pressure subjected sub-sample value. Comparing each post-pressure subjected sub-sample value to each corresponding pre-pressure subjected sub-sample value can include, for example, any kind of comparison of the values, correlation of the values, interaction of the values with each other, multiplying, dividing, adding, or subtracting the values or other mathematical manipulation of one value with the other value, or any other kind of manipulation of the values with each other.

Also at this point, a score for the original proppant sample can be determined. In an embodiment, a score for the original proppant sample can be based on the results of measuring at least one of: the amount of proppant that passes through the respective sieve for each sub-sample; and ii) the amount of proppant that remained on the respective sieve for each sub-sample. Determining a score for the original proppant sample can also be accomplished, for example, by multiplying each post-pressure subjected sub-sample value with each corresponding pre-pressure subjected sub-sample percentage to obtain a weighted average, and then adding each of the results together. An example of an embodiment of determining a score for a proppant sample, and of determining a weighted average of the amount of proppant that was crushed for each sub-sample, is shown in FIG. 4. The score of the original proppant sample can be used to determine the suitability of the proppant for use in fracking, for comparing the strength of the proppant to other proppants, or for other purposes.

Once a score for the original proppant sample has been determined, the score can be reported. For example, the score can be reported to a third party, such as a client or other individual or entity that requested that the proppant be tested.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention.

I claim:

1. A method of testing proppant comprising:
   a. obtaining a proppant sample;
   b. determining the amount of the proppant sample;
   c. combining a plurality of sieves having various mesh sizes into a stack of sieves, such that the plurality of sieves within the stack are arranged according to mesh size with the ordering of the plurality of sieves proceeding from the sieve having a largest mesh size at a top of the stack, to the sieve having a smallest mesh size at a bottom of the stack;
   d. depositing the proppant sample into the top of the stack of sieves;
   e. moving the stack of sieves;
   f. separating the proppant sample into a plurality of pre-pressure subjected sub-samples by removing the portion of the proppant sample that remained on each respective sieve of said plurality of sieves subsequent to said moving the stack of sieves, with each of the plurality of pre-pressure subjected sub-samples corresponding to the portion of the proppant sample that remained on each respective sieve of said plurality of sieves subsequent to said moving the stack of sieves;
   g. measuring the amount of each pre-pressure subjected sub-sample to determine a prepressure subjected sub-sample value for each pre-pressure subjected sub-sample;
   h. subjecting each pre-pressure subjected sub-sample to a pressure, resulting in a corresponding post-pressure subjected sub-sample for each pre-pressure subjected sub-sample;
   i. separately stacking each of said plurality of sieves over a pan, such that a distinct sieve-pan stack is formed for each of said plurality of sieves;
   j. returning each respective post-pressure subjected sub-sample to its corresponding sieve of said plurality of sieves;
   k. moving each of said distinct sieve-pan stacks; and
   l. determining a post-pressure subjected sub-sample value for each post-pressure subjected sub-sample by measuring at least one of:
      i) the amount of each post-pressure subjected sub-sample that remained on the sieve of a given distinct sieve-pan stack; and
      ii) the amount of each post-pressure subjected sub-sample that was deposited in the pan of that given distinct sieve-pan stack.

2. The method of claim 1 further comprising converting each pre-pressure subjected sub-sample value to a percentage of said amount of said proppant sample, resulting in a corresponding pre-pressure subjected sub-sample percentage for each pre-pressure subjected sub-sample value.

3. The method of claim 2 further comprising determining a score for said proppant sample by multiplying each post-pressure subjected sub-sample value with each corresponding pre-pressure subjected sub-sample percentage, and then adding each of the results together.

4. The method of claim 3 further comprising reporting the score for said proppant sample to a third party.

5. The method of claim 1 further comprising comparing each post-pressure subjected sub-sample value to each corresponding pre-pressure subjected sub-sample value.

6. A method of testing proppant comprising:
   a. obtaining a proppant sample;
   b. separating the proppant sample into a plurality of sub-samples according to grain size;
   c. subjecting each sub-sample to a pressure;
   d. independently analyzing each sub-sample; and
   e. measuring at least one of:
      i) the amount of proppant that experienced a change, if any, within each sub-sample due to said subjecting each sub-sample to a pressure; and
      ii) the amount of proppant that did not experience a change, if any, within each sub-sample due to said subjecting each sub-sample to a pressure.

7. The method of claim 6 wherein said measuring at least one of:
   i) the amount of proppant that experienced a change, if any, within each sub-sample due to said subjecting each sub-sample to a pressure; and
   ii) the amount of proppant that did not experience a change, if any, within each sub-sample due to said subjecting each sub-sample to a pressure;
further comprises determining the amount of proppant that was crushed for each sub-sample.

8. The method of claim 6 further comprising determining a score for said proppant sample based on results of said measuring at least one of:
   i) the amount of proppant that experienced a change, if any, within each sub-sample due to said subjecting each sub-sample to a pressure; and
   ii) the amount of proppant that did not experience a change, if any, within each sub-sample due to said subjecting each sub-sample to a pressure.

9. The method of claim 8 wherein said determining a score for said proppant sample further comprises determining a weighted average of the amount of proppant that was crushed for each sub-sample.

10. The method of claim 9 further comprising reporting said score for said proppant sample.

11. The method of claim 10 wherein said reporting said score for said proppant sample comprises reporting said score for said proppant sample to a third party.

12. The method of claim 6 further comprising determining the amount of proppant that was crushed for each sub-sample during said subjecting each sub-sample to a pressure.

13. The method of claim 6 wherein said subjecting each sub-sample to a pressure comprises separately subjecting each sub-sample to a pressure.

14. The method of claim 6 wherein said subjecting each sub-sample to a pressure further comprises subjecting each sub-sample to a pressure that is sufficient to crush at least a portion of the proppant within at least one of the plurality of sub-samples.

15. The method of claim 6 wherein said subjecting each sub-sample to a pressure further comprises subjecting each sub-sample to a pressure of about 6,000 pounds per square inch.

16. A method of testing proppant comprising:
   a. obtaining a proppant sample;
   b. separating the proppant sample into a plurality of sub-samples according to grain size;
   c. subjecting each sub-sample to a pressure; and
   d. independently analyzing each sub-sample to determine whether a change to the proppant occurred within each sub-sample.

17. The method of claim 16 further comprising reporting the results of said independently analyzing each sub-sample to determine whether a change to the proppant occurred within each sub-sample.

18. The method of claim 17 wherein said reporting the results comprises reporting the results to a third party.

19. The method of claim 16 wherein said separating the proppant sample into a plurality of sub-samples according to grain size comprises sieving the proppant sample over a plurality of sieves, at least two of said plurality of sieves having a different mesh size.

20. The method of claim 16 wherein said subjecting each sub-sample to a pressure further comprises subjecting each sub-sample to a pressure of about 6,000 pounds per square inch.

\* \* \* \* \*